United States Patent
Yerxa et al.

(10) Patent No.: US 6,323,187 B1
(45) Date of Patent: Nov. 27, 2001

(54) THERAPEUTIC DINUCLEOTIDE AND DERIVATIVES

(75) Inventors: Benjamin R. Yerxa, Raleigh; William Pendergast, Durham; Janet L. Rideout, Raleigh; Maryse Picher, Carrboro; Richard C. Boucher, Jr.; M. Jackson Stutts, both of Chapel Hill, all of NC (US)

(73) Assignees: Inspire Pharmaceuticals, Inc., Durham; University of North Carolina at Chapel Hill, Chapel Hill, both of NC (US)

(*) Notice: Subject to any disclaimer, the term of this patent is extended or adjusted under 35 U.S.C. 154(b) by 0 days.

(21) Appl. No.: 09/316,571

(22) Filed: May 21, 1999

Related U.S. Application Data

(60) Provisional application No. 60/086,543, filed on May 22, 1998.

(51) Int. Cl.[7] ............................. A01N 43/04; A61K 31/70
(52) U.S. Cl. ............................. 514/51; 514/42; 514/43; 514/44; 514/49; 514/52; 536/26.23; 536/25.6
(58) Field of Search ............................. 536/26.23, 25.6; 514/42, 43, 44, 49, 51, 52

(56) References Cited

U.S. PATENT DOCUMENTS

| | | |
|---|---|---|
| 5,292,498 | 3/1994 | Boucher, Jr. . |
| 5,635,160 | 6/1997 | Stutts, III et al. . |
| 5,837,861 | * 11/1998 | Pendergast et al. . |
| 5,900,407 | * 5/1999 | Pendergast et al. . |

FOREIGN PATENT DOCUMENTS

WO 98/34942    8/1998    (WO) .

OTHER PUBLICATIONS

Allegra, L., et al., "Duration of mucociliary dysfunction following antigen challenge" *J. Applied Physiol.* 55(3):726–730 (1983).
Boucher, R., et al., "Na+Transport in Cystic Fibrosis Respiratory Epithelia," *J. Clin. Invest.* 78:1245–1252 (1986).
Coste, Herve, et al., "Non–adenylylated bis(5'–nucleosidyl) tetraphosphates occur in *Saccharomyces cerevisiae* and in *Eschericia coli* and accumulate upon temperature shift or exposure to cadmium" *J. Biol. Chem.* 262(25):12096–12103 (1987).
Drutz, D., et al., "Uridine 5' Triphosphate (UTP) Regulates Mucociliary Clearance Via Purinergic Receptor Activation," *Drug Dev. Res.* 37(3):185 (1996).
Gobran, L., et al., "$P_{2u}$ purinoceptor stimulation of surfactant secretion coupled to phosphatidylcholine hydrolysis in type II cells," *Am. Physiol. Soc.* 267:L625–L633 (1994).

Klein, J., "Otitis Media," *Clin. Infect. Dis.* 19:823–833 (1994).
Lazarowski, E.R., et al., "Pharmacological selectivity of the cloned human $P_{2U}$–purinoceptor: potent activation by diadenosine tetraphosphate," *Brit. J. Pharm.* 116(1):1619–1627 (1995).
Lethem, M.I., et al., "Nucleotide Regulation of Goblet Cells in Human Airway Epithelial Explants: Normal Exocytosis in Cystic Fibrosis," *Am. J. Respir. Cell Mol. Biol.* 9:315–322 (1993).
Mason, S.J., et al., "Regulation of transepithelial ion transport and intracellular calcium by extracellular ATP in human normal and cystic fibrosis airway epithelium," *Br. J. Pharmacol.* 103:1649–1656 (1991).
Moss, A. and Parsons, V., "Current Estimates From the National Health Interview Survey," National Center for Health Statistics 10(160):66–67 (1986) DHHS Publication No. (PHS)86–1588.
Noone, P.G., et al "Effects on Cough Clearance of Aerosolized Uridine–5–'–Triphosphate ± Amiloride in Patients with primary Ciliary Dyskinesia" Abstract.
Olivier et al., "Acute Safety and Effects on Mocociliary Clearance of Aerosolized Uridine 5'–Triphosphate ± Amiloride in Normal Human Adults," *Am. J. Respir. Crit. Care Med.* 154:217–223 (1996).
Sabater, J.R., et al., "Endothelin–1 depresses tracheal mucus velocity in ovine airways via ET–A receptors,"*Am. Respir. Crit. Care Med.* 154:341–345 (1996).
Willumsen, M.J., et al., "Cellular Cl transport in cultured cystic fibrosis airway epithelium," *Am. Physiol. Soc.* 256:C1045–1053 (1989).
Wu, R., et al., "Growth and Differentiation of Human Nasal Epithelial Cells in Culture," *Am. Rev. Respir. Dis.* 132:311–320 (1985).
Yankaskas, J.R., et al., "Culture of Human Nasal Epithelial Cells on Collagen Matrix Supports," *Am. Rev. Respir. Dis.* 132:1281–1287 (1985).

* cited by examiner

*Primary Examiner*—James O. Wilson
(74) *Attorney, Agent, or Firm*—Albert P. Halluin; Viola T. Kung; Howrey Simon Arnold & White, LLP

(57) ABSTRACT

The present invention relates to $P^1$-(cytidine 5'-)-P-(uridine 5'-)tetraphosphates and its salts, esters and amides, and formulations thereof which are highly stable and selective agonists of the $P2Y_2$ and/or $P2Y_4$ purinergic receptor. The compounds of the invention are useful in the treatment of chronic obstructive pulmonary diseases such as chronic bronchitis, primary ciliary dyskinesia, cystic fibrosis, as well as prevention of pneumonia due to immobility, and the induction of sputum and its expectoration. Furthermore, because of their general ability to clear retained mucus secretions and stimulate ciliary beat frequency, the compounds of the present invention are also useful in the treatment of sinusitis and otitis media.

16 Claims, No Drawings

THERAPEUTIC DINUCLEOTIDE AND DERIVATIVES

INTRODUCTION

The application claims priority to U.S. application Ser. No. 60/086,543, filed May 22, 1998, which is incorporated herein by reference.

TECHNICAL FIELD

This invention relates to a method of enhancing clearance of secretions by increasing the hydration of retained mucus secretions, stimulating the production of mucins, and increasing ciliary beat frequency by administering $P^1$-(cytidine 5'-)-$P^4$-(uridine 5'-)-tetraphosphate ($CP_4U$) or pharmaceutically acceptable esters, amides or salts thereof.

BACKGROUND OF THE INVENTION

Chronic obstructive pulmonary disease (COPD) affects 15 million patients in the U.S. and is the sixth leading cause of death. It is characterized by the retention of mucus secretions in the lungs which results in progressive lung dysfunction over time. Many patients diagnosed with COPD have a disorder called chronic bronchitis (CB), and 600,000 patients are hospitalized each year due to an acute exacerbation of CB. Cystic fibrosis (CF) and primary ciliary dyskinesia (PCD) are other examples of lung disorders which assume a clinical profile similar to COPD. Ciliary dyskinesia, whether primary or secondary, results in retained secretions that can only be cleared by coughing. Most patients with COPD utilize coughing to help clear retained secretions because of impaired mucociliary clearance.

Another disease state characterized by the accumulation of retained mucous secretions is sinusitis. Sinusitis is an inflammation of the paranasal sinuses typically associated with an upper respiratory infection. It can occur as either an acute or chronic condition. It is this country's most common health-care complaint, affecting an estimated 31 million people. (A. Moss and V. Parsons, National Center for Health Statistics, 1986: 66–7, DHHS Publication No. (PHS)86-1588 (1985)).

Otitis media (OM) is a viral or bacterial infection of the middle ear which primarily afflicts children under the age of three. It is usually precipitated by an upper respiratory infection which spreads into the middle ear via the nasopharynx and eustachian tube. Approximately 25–50 million office visits are made each year for diagnosis and treatment of OM. By age three, about 75% of children will have had at least one episode of acute OM (J. Klein, *Clin. Infect. Dis.* 19, 823–33 (1994)). Following appropriate treatment with antibiotics, accumulated fluid in the middle ear remains, causing hearing impairment and potential language and cognitive development delays. Enhanced ability to clear secretions in the middle ear would reduce or eliminate significant sequelae of otitis media.

An additional disorder characterized by retained secretions is pneumonia. Patients who are immobilized for a variety of reasons are at high risk for developing pneumonia. Despite extra vigilance and numerous interventions, pneumonia develops in over 400,000 patients per year, with significant morbidity and mortality. Patients who require intubation and mechanical ventilation are at additional risk for ventilator associated pneumonia (VAP) due to immobility and the decrease in mucociliary clearance. The mortality rate for VAP can exceed 50% in more than 100,000 who develop VAP each year.

There are also situations where it is therapeutically desirable to increase drainage of the lacrimal system. When the lacrimal drainage system is not functioning properly the result can be excessive tearing (epiphora), mucopurulent discharge, and recurrent dacryocystitis. Current treatments for nasolacrimal duct obstruction are mostly invasive surgical procedures, and researchers have sought to discover noninvasive pharmaceutical treatments.

Tear secretion can be stimulated from lacrimal accessory tissues via $P2Y_2$ and/or $P2Y_4$ purinergic receptor-mediated mechanisms similar to those which hydrate airway epithelia. Dry eye disease is the general term for indications produced by abnormalities of the precorneal tear film characterized by a decrease in tear production or an increase in tear film evaporation, together with the ocular surface disease that results. Currently, the pharmaceutical treatment of dry eye disease is mostly limited to administration of artificial tears (saline solution) to temporarily rehydrate the eyes. However, relief is short lived and frequent dosing is necessary.

Normally, mucous secretions are removed via the mucociliary clearance (MCC) system. MCC relies on the integrated action of three components: 1) mucus secretion by goblet cells and submucosal glands; 2) the movement of cilia on epithelial cells which propels the mucus across the luminal surface; and 3) ion transport into and out of luminal epithelial cells which concomitantly controls the flow of water into the mucus.

It is now known that nucleoside phosphates such as uridine 5'-triphosphate (UTP) modulate all of the components of the MCC system. First, UTP has been shown to increase both the rate and total amount of mucin secretion by goblet cells in vitro (M. Lethem, et al., *Am J. Respir. Cell Mol. Biol.* 9, 315–22 (1993)). Second, UTP has been shown to increase cilia beat frequency in human airway epithelial cells in vitro (D. Drutz, et al., *Drug Dev. Res.* 37(3), 185 (1996)). And third, UTP has been shown to increase $Cl^-$ secretion, and hence, water secretion from airway epithelial cells in vitro (S. Mason, et al., *Br. J. Pharmacol.* 103, 1649–56 (1991)). In addition, it is thought that the release of surfactant from Type II alveolar cells in response to UTP (Gobran, *Am. J. Physiol.* 267, L625–L633 (1994)) contributes to optimal functioning of the lungs and may assist in maximizing MCC. UTP has been shown to increase intracellular $Ca^{++}$ due to stimulation of phospholipase C by the $P2Y_2$ receptor (H. Brown, et al., *Mol. Pharmocol.* 40, 648–55 (1991)).

UTP's modulation of all components of the mucociliary escalator system results in improvement in lung mucociliary clearance in normal volunteers without any significant side-effects (K. Olivier, et al., *Am J. Respir. Crit. Care Med.* 154, 217–23 (1996)). In addition, UTP significantly enhances cough clearance (clearance of retained secretions by coughing) in patients with PCD (P. Noone, et al., *Am. J. Respir. Crit. Care Med.* 153, A530 (1996)). The dinucleotide, $P^1,P^4$-di(uridine-5'-)tetraphosphate, has also been shown to increase sputum production in normal healthy volunteers, indicating an enhancement of MCC.

Because of UTP's demonstrated ability to increase the clearance of retained mucous secretions, applicants were motivated to investigate other nucleoside phosphates in order to maintain or improve therapeutic efficacy while increasing stability. During the course of this investigation, it was found that $CP_4U$, unlike the other cytidine-containing dinucleoside tetraphosphate $C_2P_4$, possessed surprising potency at the $P2Y_2$ and $P2Y_4$ receptors. Additionally, it was observed that $CP_4U$ had unexpectedly considerably enhanced resistance toward biological degradation, as evidenced by its stability in biological preparations. The present invention is based upon the potency and increased duration of action of CP$_4$U in respiratory therapies due to its increased biological stability.

SUMMARY OF THE INVENTION

A method of enhancing secretion clearance by hydrating mucous and increasing ciliary beat frequency in a subject in need of such treatment is disclosed. The method comprises administering to the patient a compound of Formula I:

Formula I

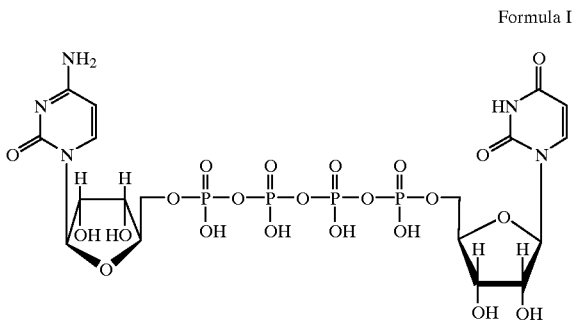

or pharmaceutically acceptable salts, esters or amides thereof.

Novel esters and amides of the compound of Formula I are also disclosed.

The compounds of Formula I are highly stable and selective agonists of the P2Y$_2$ and/or P2Y$_4$ purinergic receptor; thus, they are useful in the treatment of chronic obstructive pulmonary diseases such as chronic bronchitis, PCD, and cystic fibrosis; they are also useful in the treatment of immobilized patients who are at risk for developing pneumonia. Furthermore, because of their general ability to clear retained mucus secretions and stimulate ciliary beat frequency, the compounds of the present invention are useful in the treatment of sinusitis and otitis media. The compounds of Formula I are also useful for facilitating the expectoration of a sputum specimen for diagnostic purposes in patients at risk for lung cancer, pneumonia, and other infectious diseases. Additionally, it is postulated that the compounds of Formula I could be an adjunct in the treatment of asthma. They could also enhance the performance of athletes by increasing the clearance of mucous secretions from the lungs. The compounds of Formula I may also be useful for wound healing.

DETAILED DESCRIPTION OF THE INVENTION

Figure 1:
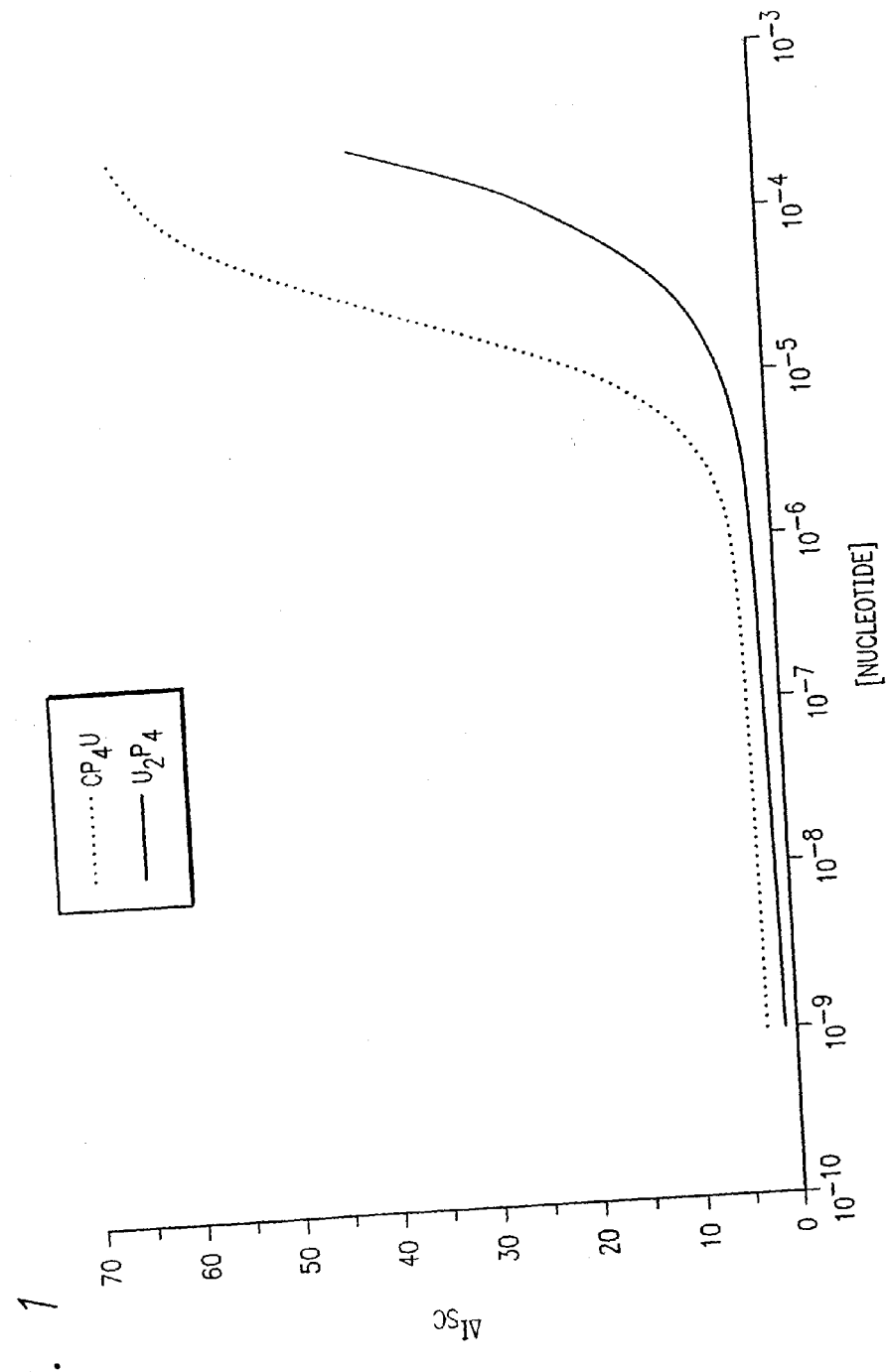
FIG. 1 illustrates the change in chloride ion diffusion potentials ($\Delta I_{SC}$, change in short circuit potential) in human nasal epithelial cells when U$_2$P$_4$ or CP$_4$U was added to the cell surface medium.

The invention provides a method of clearing retained mucous secretion and enhancing ciliary beat frequency in a subject in need of such treatment. The method comprises administering to the patient a compound of Formula I.

Formula I

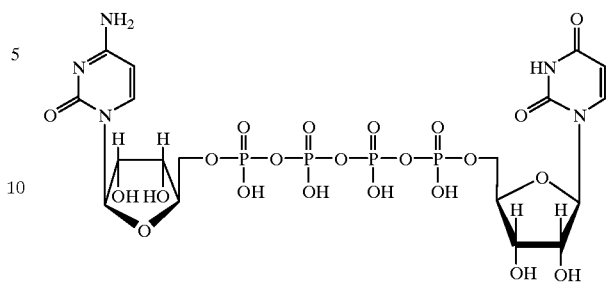

or pharmaceutically acceptable salts, esters or amides thereof.

The compounds of Formula I, including its salts, esters and amides, will hereinafter be referred to as "the compounds of the present invention."

The compounds of the present invention encompass pharmaceutically acceptable salts, such as, but not limited to, an alkali metal salt such as sodium or potassium; an alkaline earth metal salt such as magnesium or calcium; manganese; or an ammonium or tetraalkyl ammonium salt, i.e., NX$_4^+$ (wherein X is C$_{1-4}$ alkyl). Pharmaceutically acceptable salts are salts that retain the desired biological activity of the parent compound and do not impart undesired toxicological effects. Salts of the present invention encompass mono-, di-, tri- and tetra-cations which may contain a single cation or mixed cations.

The present invention also provides novel acylated prodrugs (e.g., esters and amides) of the compound disclosed herein. Preferred esters of the invention include carboxylic acid esters in which the non-carbonyl moiety of the ester grouping is selected from straight or branched chain alkyl such as n-propyl, t-butyl; n-butyl, alkoxyalkyl (e.g. methoxymethyl), aralkyl (e.g. benzyl), aryloxyalkyl (e.g. phenoxymethyl), and aryl (e.g. phenyl); sulfonate esters such as alkyl- or aralkylsulfonyl (e.g. methanesulfonyl); amino acid esters (e.g. L-valyl or L-isoleucyl); dicarboxylic acid esters (e.g. hemisuccinate). The phosphate esters may be further esterified by, for example, a C$_{1-20}$ alcohol or by a 2,3-di(C$_{6-24}$)acyl glycerol. Any alkyl moiety present in such esters contains 1 to 18 carbon atoms, particularly 1 to 4 carbon atoms. Alkyl groups containing 3–18 carbon atoms may be saturated or unsaturated. Any aryl moiety present in such esters advantageously comprises a phenyl group optionally substituted, e.g. by halogen, C$_{1-4}$ alkyl, C$_{1-4}$ alkoxy, nitro, or hydroxyl. The above-mentioned pharmaceutically accepted amides of the invention include those derivatives wherein the cytosine amino group is in the form of an amide, e.g. NHCOR wherein R is C$_{1-4}$ alkyl or aryl (e.g. phenyl optionally substituted by halogen, C$_{1-4}$ alkyl, C$_{1-4}$ alkoxy, nitro or hydroxyl).

The compounds of the present invention are highly selective agonists of the P2Y$_2$ and/or P2Y$_4$ purinergic receptor; thus, they are useful in the treatment of mammals including humans suffering from chronic obstructive pulmonary diseases such as chronic bronchitis, acute bronchitis, acute exacerbations of chronic bronchitis, PCD, cystic fibrosis, as well as prevention of pneumonia due to immobility. In instances where cilia are impaired or absent, the compounds of the present invention enhance cough clearance. Furthermore, because of their general ability to clear retained mucus secretions and stimulate ciliary beat frequency, the compounds of the present invention are useful in the treatment of acute and chronic sinusitis and otitis media in mammals, including humans. By enhancing secretion clearance, the compounds are useful as protection before or after exposure to inhaled biological warfare agents. They can also be used to enhance lung imaging by clearing secretions from the lungs prior to obtaining the image.

Because of their surprisingly increased biological stability, the compounds of the present invention provide increased duration of action for respiratory therapies. This improvement in stability offer advantages in the treatment of both acute and chronic respiratory disorders.

Esters and amides of the compound of Formula I are useful for treating ophthalmic disorders such as dry eye and retinal detachment. They are also useful for increasing drainage of the lacrimal system.

Though the compounds of the present invention are primarily concerned with the treatment of human subjects, they may also be employed for the treatment of other mammalian subjects such as dogs, cats and horses for veterinary purposes.

The compounds of the present invention may be administered orally, topically, parenterally, by inhalation or spray, intra-operatively, rectally, or vaginally in dosage unit formulations containing conventional non-toxic pharmaceutically acceptable carriers, adjuvants and vehicles. The term topically as used herein includes patches, gels, creams, ointments, liquid irrigation, or nose, eye or ear drops. The term parenteral as used herein includes subcutaneous injections, intravenous, intramuscular, intrasternal injection or infusion techniques.

In another aspect of the invention, there is provided a pharmaceutical formulation comprising a compound of the present invention and a pharmaceutically acceptable carrier. One or more compounds of the invention may be present in association with one or more non-toxic pharmaceutically acceptable carriers or diluents or adjuvants and, if desired, other active ingredients. One such carrier would be sugars, where the compounds may be intimately incorporated in the matrix through glassification or simply admixed with the carrier (e.g., lactose, sucrose, trehalose, mannitol) or other acceptable excipients for lung or airway delivery.

The compounds of the present invention may be administered separately or together with mucolytics such as DNAse or acetylcysteine, or with radiolabeled substances.

The pharmaceutical compositions containing a compound of the present invention may be in a form suitable for oral use, for example, as tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous formulations contain the active materials in admixture with excipients suitable for manufacture. Such excipients are suspending agents, for example: sodium carboxymethylcellulose, methylcellulose and sodium alginate. Dispersing or wetting agents may be a naturally-occurring phosphatide or condensation products of an alkylene oxide with fatty acids, or condensation products of ethylene oxide with long chain aliphatic alcohols, or condensation products of ethylene oxide with partial esters from fatty acids and a hexitol, or condensation products of ethylene oxide with partial esters derived from fatty acids and hexitol anydrides. Those skilled in the art will recognize the many specific excipients and wetting agents encompassed by the general description above. The aqueous formulations may also contain one or more preservatives, for example, ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

The compounds of the present invention may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle. The sterile injectable preparation may be a sterile injectable solution or suspension in a non-toxic parentally acceptable diluent or solvent. Among the acceptable vehicles and solvents that may be employed are sterile water, saline solution, or Ringer's solution.

The compounds of the present invention may also be administered in the form of suppositories for ear, rectal or vaginal administration of the drug. These compositions can be prepared by mixing the drug with a suitable non-irritating excipient which is solid at ordinary temperatures but liquid at body temperature and will therefore melt in the body to release the drug. Such materials are cocoa butter and polyethylene glycols.

Solutions of compounds of the present invention may be administered by intra-operative installation, using such methods as irrigation, lavage, topical application, injection or other method known to those skilled in the art.

For treatment of respiratory disorders, concentration levels from about $10^{-7}$ M to about $10^{-1}$ M, preferably $10^{-5}$ to $10^{-3}$ M, or doses of about 1–400 mg, may be used. For ophthalmic and sinus uses, 0.1 to 10.0% concentrations may be used. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound, the age, body weight, general health, sex, diet, time of administration, route of administration, and rate of absorption, distribution, metabolism and excretion, drugs used in combination, and the type and severity of the particular disease undergoing therapy.

The compounds encompassed by the present invention may be prepared by condensation of uridine mono-, di-, or triphosphate, activated with a condensing agent such as, but not limited to, carbonyldiimidazole or dicyclohexylcarbodiimide, with cytidine mono-, di-, or triphosphate to form the desired dinucleotide tetraphosphate ($P_1$-(cytidine 5'-)$P_4$-(uridine 5'-)tetraphosphate); or by condensation of a similarly activated cytidine mono-, di-, or triphosphate with uridine mono-, di-, or triphosphate. Analogous procedures yield $N^4$-amido derivatives of ($P_1$-(cytidine 5'-)uridine 5'-)tetraphosphate. Nucleoside phosphates used as starting materials may be commercially available (Sigma) or may be made from the corresponding nucleosides by methods well known to those skilled in the art. Likewise, where nucleosides are not commercially available, they may be made by modification of other readily available nucleosides, or by synthesis from heterocyclic and carbohydrate precursors by methods well known to those skilled in the art.

Those skilled in the art will recognize additional synthetic methodologies which may be employed to prepare pharmaceutically acceptable salts and acylated prodrugs of the compound of Formula I. Thus salts may be prepared utilizing cation exchange resins. Esters and amides, for example, may be made by reaction of the desired hydroxy or amino compound with the appropriate acid, activated with carbonyldiimidazole, dicyclohexylcarbodiimide or other suitable condensing agent, or with an acid anhydride or acid chloride with or without a basic catalyst such as a tertary amine, quaternary ammonium salt or an inorganic base.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

Preparation of $P^1$-(Cytidine 5'-)-$P^1$-(uridine 5'-) tetraphosphate, tetrammonium salt Uridine 5'-monosphate, tributylamine salt was prepared by dissolving uridine 5'-monophosphate, free acid (Sigma) (3.0 g) with tributylamine (2.0 mL) in DMF to make a 0.34M solution. An anhydrous DMF solution of uridine 5'-monophosphate tributylamine salt (5.6 ml, 1.89 mmol, 0.34 M) was added to a 10 ml round bottomed flask under $N_2$ and carbonyldiimidazole (459 mg, 2.83 mmol) was added and the solution stirred at 25° C. for 30 min. A DMF solution of cytidine 5'-triphosphate tributylamine salt, prepared by treating the trisodium salt with Dowex 50H$^+$ resin followed by tributylamine in DMF was added and the reaction mixture stirred at 65° C. for 3 h. The solution was evaporated in vacuo and purified two times by column chromatography (DEAE Sephadex; $H_2O \rightarrow 0.3M$ $NH_4HCO_3$ gradient). The pure fractions were concentrated in vacuo at 35° C., and $H_2O$ added and reevaporated ten times to obtain a white solid (203 mg): $^1H$ NMR ($D_2O$, TMS) δ4.1 (m, br, 6H), 4.2 (m, 4H), 5.8 (m, 3H), 5.95 (m, 1H), 7.7 (m, 2H); $^{31}P$ NMR ($D_2O$, $H_3PO_4$ std) δ–22.4 (m, 2P), –10.6 (m, 2P); Exact mass calc for $C_{18}H_{26}N_5O_{22}P_4$ (M–H)=788.0020, found 787.9985.

EXAMPLE 2

Preparation of $P^1$-(Cytidine 5'-)-$P^1$-(uridine 5'-) tetraphosphate, tetrammonium salt A solution of uridine 5'-triphosphate (UTP) trisodium salt (5.86g, 0.01 mol) in water (5 mL) was placed onto a column of BioRad AG-MP 50 strong cation exchange resin in its pyridinium form (50 mL bed volume) and eluted with distilled water (about 300 mL) into a flask containing tributylamine (5.55 g 0.03 mol). The suspension was shaken with ethanol (50 mL) and the mixture set aside in the refrigerator overnight. The solution was filtered to remove a little oily residue, evaporated to dryness under reduced pressure, and the residue dried for 1 h at 0.08 mm Hg at room temperature. The residue was dried by evaporation with 2×20 mL of anhydrous dimethylformamide (DMF) at 0.1 mm Hg. The resulting anhydrous tributylamine salt was made up to 100 mL with anhydrous acetone to yield a stock solution (0.1 M in UTP). Dicyclohexylcarbodiimide(DCC) (Baker, 1.0 g, 5.0 mmol) was added to an aliquot of the foregoing UTP solution (10 mL, 1 mmol) and the solution stirred at room temperature for 30 min. The deposited dicyclohexylurea was removed by filtration, the reaction mixture extracted with hexane (100 mL), and the residue dissolved in dry deuterated dimethylsulfoxide (DMSO-$d_6$, 3.0 mL). This solution of uridine 5'-cyclic metaphosphate (UcTP) was added to the tributylamine salt of cytidine 5'-monophosphate (CMP), prepared by addition of tributylamine (0.714 mL, 3 mmol) to CMP free acid (Sigma, 0.65 g, 2 mmol), and the suspension stirred at 50° C. for 24 h. The reaction mixture was evaporated under high vacuum overnight, the residue dissolved in water (5 mL) and separated by semipreparative ion-exchange chromatography (Hamilton PRP X-100 column, eluting with isocratic 1.0 M ammonium bicarbonate, 8 mL/min, 30 min, multiple injections of 500 μL). The dinucleotide tetraphosphate eluted between 31 and 37 min; fractions containing the product were evaporated repeatedly with water and the residue lyophilized to yield the title compound (59 mg) as a white solid. $^1H$ NMR $D_2O$, δ ppm from tetramethylsilane: 4.10–4.13 (m, 6H) 4.17–4.26 (m, 4H); 5.815 (d, J=7.8 Hz, 1H); 5.82 (d, J=5.0 Hz, 2H); 6.082 (d, J=7.7 Hz, 1H); 7.80 (d, J=7.8 Hz, 1H); 7.91 (d, J=8.2 Hz, 1H). $^{31}P$ NMR ($D_2O$ δ ppm from $H_3PO_4$): –22.45 (m, 2P); –10.80 (m, 2P).

EXAMPLE 3

Pharmacological Activity as Measured by the Inositol Phosphate Assay

The pharmaceutical utility of the compounds of this invention is indicated by the inositol phosphate assay for $P2Y_2$ and other P2Y receptor activity. This widely used assay, as described in E. Lazarowski, et al., *Brit. J. Pharm.* 116, 1619–27 (1995), relies on the measurement of inositol phosphate formation as a measurement of activity of compounds activating receptors linked via G-proteins to phospholipase C.

The compounds of Formula I was tested for its ability to elicit $P2Y_1$, $P2Y_2$, $P2Y_4$ and $P2Y_6$ receptor activity using the inositol phosphate assay as described by E. Lazarowski, et al., *Brit. J. Pharm.* 116, 1619–27 (1995). The results for CP$_4$U and the all cytidine-containing dinucleotide, C$_2$P$_4$, are summarized in Table I below.

TABLE I

| Compound | Activity Summary EC$_{50}$'s ($\mu$mol) | | | |
|---|---|---|---|---|
| | P2Y$_1$ | P2Y$_2$ | P2Y$_4$ | P2Y$_6$ |
| C$_2$P$_4$ | IA* | IA* | IA* | IA* |
| CP$_4$U | IA* | 0.45 | 0.65 | 3.5 |

*IA = Inactive (i.e. no agonist activity at 30 $\mu$M)

In this assay, CP$_4$U showed surprising activity at the P2Y$_2$ and P2Y$_4$ receptors, compared to the all cytidine dinucleotide analog, C$_2$P$_4$.

EXAMPLE 4

Induction of chloride secretion in vivo facilitates hydration of thickened airway mucus secretions in diseases where patients will benefit from mobilization and clearance of such secretions. Activation of an apical non-CFTR chloride channel induces efflux of chloride ions and water that help rehydrate the lung secretions (Boucher, U.S. Pat. No. 5,292,498 and Boucher, et al U.S. Pat. No. 5,635,160 and references therein).

Chloride Secretion in Human Nasal Airway Cells

Airway epithelial cells were desegregated and isolated from freshly excised human nasal surgical specimens (Yankaskas, et al., *Am. Rev. Respir. Dis.* 132, 1281–1287 (1985)). Confluent monolayers were cultured on permeable collagen matrix supports in F-12 hormone-supplemented medium (Wu, et. al., *Am. Rev. Respir. Dis.* 132, 311–320 (1985)). Cells were incubated at 37° C. and grown to confluence. Development of transepithelial resistance was monitored to determine the formation of tight junctions between the cells. After formation of tight junctions, was confirmed, the matrix supports containing the cultures were mounted in modified Using chambers.

Cultured human airway epithelia were mounted in Using chambers with a submucosal bath of Krebs bicarbonate Ringer [KBR (in mM) 140 Na$^+$, 120 Cl$^-$ 5.2 K$^+$, 25 HCO$_3^-$, 2.4 HPO$^{2-}_4$, 0.4 HPO$_4^-$; 1.1 Ca$^{2+}$, 1.2 Mg$^{2+}$, and 5.2 glucose]. The luminal surface was bathed by KBr or by a high K$^+$, low Cl$^-$ (HKLC) Ringers [(in mM) 40 Na$^+$, 100 K$^+$, 4.5 Cl$^-$, 120 gluconate, 25 HCO$_3^-$, 2.4 HPO$^{2-}_4$ 0.4 HPO$_4^-$, 1.1 Ca$^{2+}$, 1.2 Mg$^{2+}$, and 5.2 gluclose].

Polycarbonate Using chambers were milled to fit the plastic cups that supported the permeable collagen matrix on which the cells were grown. Bioelectric properties including I$_{SC}$, transepithelial potential difference and resistance were monitored. Short-circuit current (I$_{SC}$) was measured with a digital voltmeter (UNC Electronics, Chapel Hill, N.C.) and plotted on a strip-chart recorder. The open circuit potential was recorded periodically, and conductance was monitored in the voltage clamp mode by the current deflection in response to a 10-mV voltage pulse.

A stable baseline of I$_{SC}$ was recorded and amiloride (100 $\mu$M) was added to the solution bathing the apical surface to block sodium absorption. The residual I$_{SC}$ measured under these conditions was a good approximation of chloride secretion (Boucher, et al., *J. Clin. Invest.* 78, 1245–1252 (1986); Willumsen, et al., *Am. J. Physiol.* 256, C226–233, C1033–C1044, C1045–C1053 (1989)). After recording a stable baseline, a solution of the test compound was added to the chamber bathing the apical surface of the epithelial culture. The change in I$_{SC}$ was recorded. Concentration-response curves were obtained by cumulative addition of higher concentrations of the test compound in 0.5 log steps.

FIG. 1 of Example 4 shows the change in chloride ion diffusion potentials ($\Delta$I$_{SC}$, change in short circuit potential) in human nasal epithelial cells when U$_2$P$_4$ or CP$_4$U was added to the cell surface medium. The results show that CP$_4$U is approximately ten-fold more potent than the all uridine-containing dinucleotide, U$_2$P$_4$ in the chloride secretion assay.

EXAMPLE 5

Metabolic Stability as Measured by Incubation on Human Airway Cells

The compound of Formula I (CP$_4$U) was tested for its ability to resist metabolism by enzymes present on the surface of cultured human bronchial (airway) epithelial cells and the results compared to the dinucleotide U$_2$P$_4$ (P$^1$,P$^4$-Di(uridine 5'-)tetraphosphate) and the nucleoside triphosphate, UT (uridine 5'-triphosphate). Epithelial cells were grown as monolayers on an airliquid interface in ALI medium. Assays were conducted on fully differentiated cells in KRB-Ringer solution (pH 7.2) at 37° C. with 0.1 mM nucleotide substrate. Aliquots of airway surface liquid were removed at 5, 10, 15, 20, 40 and 60 minutes. The metabolism was stopped by boiling and filtering the aliquots, and the samples were analyzed by high performance liquid chromatography using the following conditions: C- 18 column with a 55 min gradient of 10–100 mM KH$_2$PO$_4$ and constant 8 mM tetrabutyl ammonium hydrogen sulfate and 10% methanol).

Figure 2:
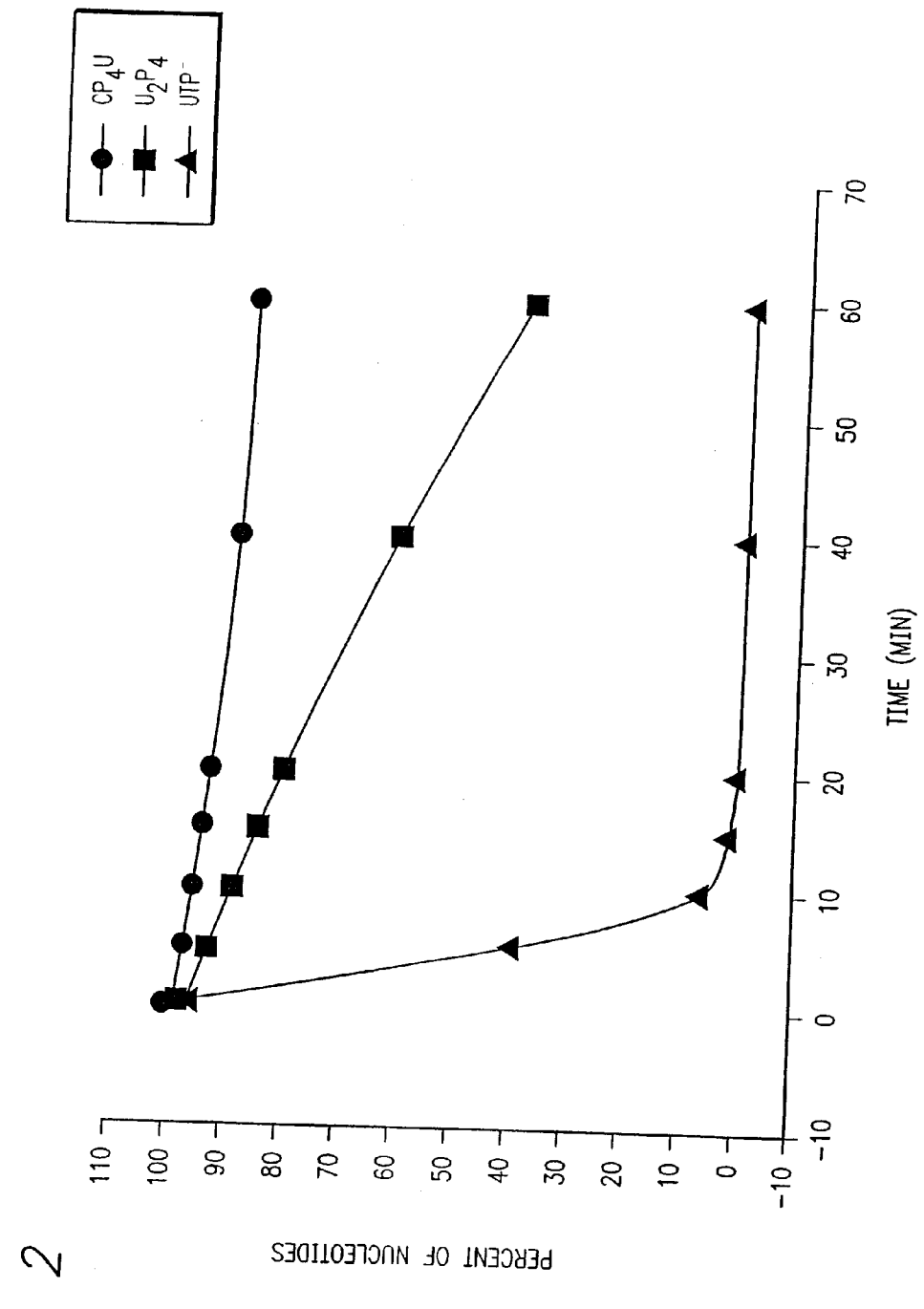
FIG. 2 illustrates the comparative rates of hydrolysis of CP$_4$U, U$_2$P$_4$, and UTP by human bronchial epithelial cells.

The results are presented in FIG 2. The compound of Formula I, CP$_4$U, showed unexpected stability compared to the other nucleotides, UTP and U$_2$P$_4$. CP$_4$U was not metabolized over a 60 minute period, whereas UTP and U$_2$P$_4$ were degraded by 100 and 40%, respectively.

The compound that is the subject of the invention was tested in an animal model (L. Allegra, et. al., *J. Applied Physiol.*, 55 (3) 726–730 (1983); J. R. Sabater, et. al., *Am. Respir. Crit. Care Med.*, 154, 341–345 (1996)). Nebulized compound stimulated tracheal mucus velocity (TMV) when compared to vehicle control. TMV is a measure of mucociliary clearance in a single large airway.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of Formula I,

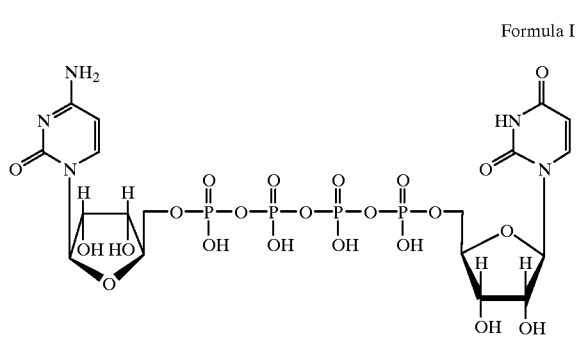

Formula I in a form of a pharmaceutically acceptable salt, ester or amide thereof.

2. A pharmaceutical composition comprising a compound of Formula I,

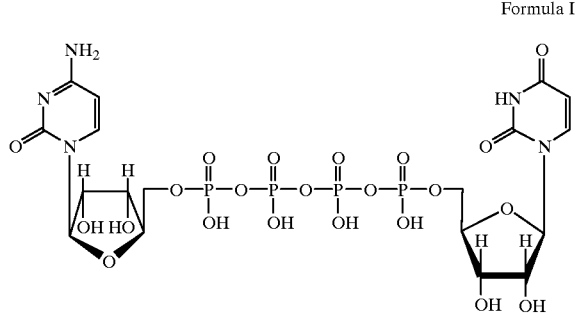

Formula I in a form of a pharmaceutically acceptable salt, ester or amide thereof together with a pharmaceutically acceptable carrier therefor.

3. The amide of the compound of Formula I as described in claim 1, wherein the cytosine amino group is NHCOR wherein R is $C_{1-6}$ alkyl, phenyl or phenyl substituted by halogen, $C_{1-4}$ alkyl, $C_{1-4}$ alkoxy, nitro or hydroxyl.

4. The ester of the compound of Formula I as described in claim 1, wherein said ester is selected from a carboxylic acid ester, a dicarboxylic acid ester, a sulfonate ester, a phosphate ester or an amino acid ester.

5. $P^1$-(Cytidine-5'-)-$P^4$-(uridine 5'-)tetraphosphate tetrammonium salt.

6. A method of enhancing secretion clearance and enhancing ciliary beat frequency in a mammal in need of such treatment by administering to said mammal a compound of Formula I:

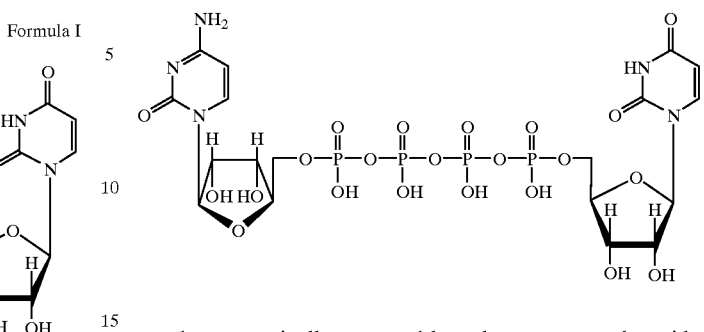

Formula I or pharmaceutically acceptable salts, esters and amides thereof.

7. A method of treating chronic obstructive pulmonary diseases in a mammal by administering an effective amount of a compound of Formula I as described in claim 1 to enhance secretion clearance and removal.

8. A method of treating acute and chronic sinusitis in a mammal by administering an effective secretion clearing amount of a compound of Formula I as described in claim 1.

9. A method of facilitating the expectoration of a deep sputum specimen in a mammal by administering an amount of a compound of Formula I as described in claim 1 effective to facilitate expectoration of a sample.

10. A method of enhancing cough clearance by administering an effective amount of a compound of Formula I as described in claim 1.

11. A method of enhancing lung imaging by administering an amount of a compound of Formula I as described in claim 1 effective to clear secretions from the lungs prior to obtaining the image.

12. A method of preventing pneumonia in a mammal by administering to said mammal an amount of a compound of Formula I, as described in claim 1, effective to enhance clearance of secretions.

13. A method of treating otitis media in a mammal by administering to said mammal an effective amount of a compound of Formula I as described in claim 1.

14. A method of enhancing clearance of respired biological warfare agents in a mammal by administering to said mammal an effective amount of a compound of Formula I as described in claim 1.

15. A method of treating dry eye disease in a mammal by administering to said mammal an effective amount of an ester or amide of Formula I, as described in claim 1.

16. A method of treating retinal detachment in a mammal by administering to said mammal an effective amount of an ester or amide of Formula I, as described in claim 1.

* * * * *

UNITED STATES PATENT AND TRADEMARK OFFICE
CERTIFICATE OF CORRECTION

PATENT NO.    : 6,323,187 B1  
DATED         : November 27, 2001  
INVENTOR(S)   : Benjamin R. Yerxa et al.

It is certified that error appears in the above-identified patent and that said Letters Patent is hereby corrected as shown below:

Drawings,
Before Column 1, insert Figure 1 and Figure 2 as attached herewith.

Signed and Sealed this

Twenty-seventh Day of August, 2002

Attest:

JAMES E. ROGAN  
Director of the United States Patent and Trademark Office

Attesting Officer

UNITED STATES PATENT AND TRADEMARK OFFICE
CERTIFICATE OF CORRECTION

PATENT NO. : 6,323,187 B1  Page 1 of 1
DATED : November 27, 2001
INVENTOR(S) : Benjamin R. Yerxa et al.

It is certified that error appears in the above-identified patent and that said Letters Patent is hereby corrected as shown below:

<u>Drawings,</u>
Before Column 1, insert Figure 1 and Figure 2 as attached herewith.

This certificate supersedes Certificate of Correction issued August 27, 2002.

Signed and Sealed this

Twenty-sixth Day of November, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,323,187 B1
DATED         : November 27, 2001
INVENTOR(S)   : Benjamin R. Yerxa et al.

It is certified that error appears in the above-identified patent and that said Letters Patent is hereby corrected as shown below:

Drawings,
Before Column 1, insert Figure 1 and Figure 2 as attached herewith.

This certificate supersedes Certificate of Correction issued August 27, 2002, and November 26, 2002.

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,323,187 B1
DATED : November 27, 2001
INVENTOR(S) : Benjamin R. Yerxa et al.

It is certified that error appears in the above-identified patent and that said Letters Patent is hereby corrected as shown below:

Column 1,
Line 3, insert
-- GOVERNMENT RIGHTS
This invention was made in part with government support under a National Institute of Health Grant HL34322. The government has certain rights to this invention. --

Signed and Sealed this

Nineteenth Day of October, 2004

JON W. DUDAS
*Director of the United States Patent and Trademark Office*